(12) United States Patent
McMains

(10) Patent No.: US 11,109,979 B2
(45) Date of Patent: Sep. 7, 2021

(54) EXPANDABLE INTERBODY DEVICE

(71) Applicant: Michael Craig McMains, Carmel, IN (US)

(72) Inventor: Michael Craig McMains, Carmel, IN (US)

(\*) Notice: Subject to any disclaimer, the term of this patent is extended or adjusted under 35 U.S.C. 154(b) by 0 days.

(21) Appl. No.: 16/970,490

(22) PCT Filed: Feb. 19, 2019

(86) PCT No.: PCT/US2019/018594
§ 371 (c)(1),
(2) Date: Aug. 17, 2020

(87) PCT Pub. No.: WO2019/161393
PCT Pub. Date: Aug. 22, 2019

(65) Prior Publication Data
US 2020/0368037 A1 Nov. 26, 2020

Related U.S. Application Data

(60) Provisional application No. 62/710,481, filed on Feb. 16, 2018.

(51) Int. Cl.
*A61F 2/44* (2006.01)
*A61F 2/30* (2006.01)

(52) U.S. Cl.
CPC .. *A61F 2/4425* (2013.01); *A61F 2002/30281* (2013.01); *A61F 2002/30365* (2013.01);
(Continued)

(58) Field of Classification Search
CPC .......... A61F 2/4425; A61F 2002/30281; A61F 2002/30365; A61F 2002/30523; A61F 2002/30556; A61F 2002/443
(Continued)

(56) References Cited

U.S. PATENT DOCUMENTS 6,676,703 B2  1/2004  Biscup
8,282,683 B2  10/2012 McLaughlin
(Continued)

FOREIGN PATENT DOCUMENTS

WO  WO 2009/064787  *  5/2009 ............... A61B 2/44
WO  WO 2009/064787 A2  5/2009

OTHER PUBLICATIONS

International Search Report issued in PCT/US2019/018594 dated Apr. 30, 2019 (pp. 3).
(Continued)

*Primary Examiner* — Jessica Weiss
(74) *Attorney, Agent, or Firm* — Woodard, Emhardt, Henry, Reeves & Wagner, LLP

(57) ABSTRACT

Disclosed is an expandable interbody device that includes a support structure having a top side and a bottom side, a top plate positioned on the top side of the support structure, a bottom plate positioned on the bottom side of the support structure, a gear rotatably connected to the support structure, wherein the gear is rotatable relative to the support structure, a first rack that is operationally coupled to the top plate, wherein the first rack is operationally connected to the gear such that rotating the gear in an opening direction moves the top plate away from the support structure by moving the first rack relative to the gear, and a second rack that is operationally coupled to the bottom plate, wherein the second rack is operationally connected to the gear such that rotating the gear in an opening direction moves the bottom plate away from the support structure by moving the second rack relative to the gear.

24 Claims, 14 Drawing Sheets

(52) U.S. Cl.
CPC ............... *A61F 2002/30523* (2013.01); *A61F 2002/30556* (2013.01); *A61F 2002/443* (2013.01)

(58) Field of Classification Search
USPC .......................................... 623/17.11–17.16
See application file for complete search history.

(56) References Cited

U.S. PATENT DOCUMENTS

| | | |
|---|---|---|
| 8,308,802 B2 | 11/2012 | Rhoda |
| 8,328,818 B1 | 12/2012 | Seifert |
| 8,657,882 B2 | 2/2014 | Bonin, Jr. |
| 8,876,905 B2 | 11/2014 | Frasier |
| 8,940,049 B1 | 1/2015 | Jimenez |
| 9,198,772 B2 | 12/2015 | Weiman |
| 9,445,920 B2 | 9/2016 | Baynham |
| 9,700,430 B2 | 7/2017 | Perrow |
| 10,722,380 B1 * | 7/2020 | Berry .................... A61F 2/4455 |
| 2004/0015315 A1 | 8/2004 | Cohen et al. |
| 2004/0153156 A1 | 8/2004 | Cohen et al. |
| 2007/0250172 A1 * | 10/2007 | Moskowitz ............ A61B 17/68 623/17.15 |
| 2010/0185291 A1 | 7/2010 | Jimenez et al. |
| 2011/0015747 A1 * | 1/2011 | McManus ................. A61F 2/44 623/17.16 |
| 2011/0251692 A1 * | 10/2011 | McLaughlin ......... A61F 2/4455 623/17.16 |
| 2014/0194991 A1 | 7/2014 | Jimenez |
| 2014/0207236 A1 * | 7/2014 | Prevost ................... A61F 2/442 623/17.16 |
| 2014/0316522 A1 * | 10/2014 | Weiman ................ A61F 2/4611 623/17.16 |
| 2015/0094814 A1 | 4/2015 | Emerick |
| 2017/0165082 A1 | 6/2017 | Faulhaber |
| 2017/0239062 A1 | 8/2017 | Williams |
| 2018/0360616 A1 * | 12/2018 | Luu ....................... A61F 2/4425 |
| 2020/0368036 A1 * | 11/2020 | Hessler ................ A61F 2/4425 |

OTHER PUBLICATIONS

Written Opinion issued in related PCT/US2019/18594 dated Apr. 19, 2019 (pp. 8).

* cited by examiner

EXPANDABLE INTERBODY DEVICE

CROSS-REFERENCE TO RELATED APPLICATIONS

This application is a national stage application of PCT/US2019/018594 filed Feb. 19, 2019, which claims the benefit of U.S. Provisional Application No. 62/710,481, filed Feb. 16, 2018, which are both hereby incorporated by reference.

BACKGROUND

This disclosure is in the field of expandable interbody devices.

DESCRIPTION OF THE ILLUSTRATED EMBODIMENTS

Figure 1:
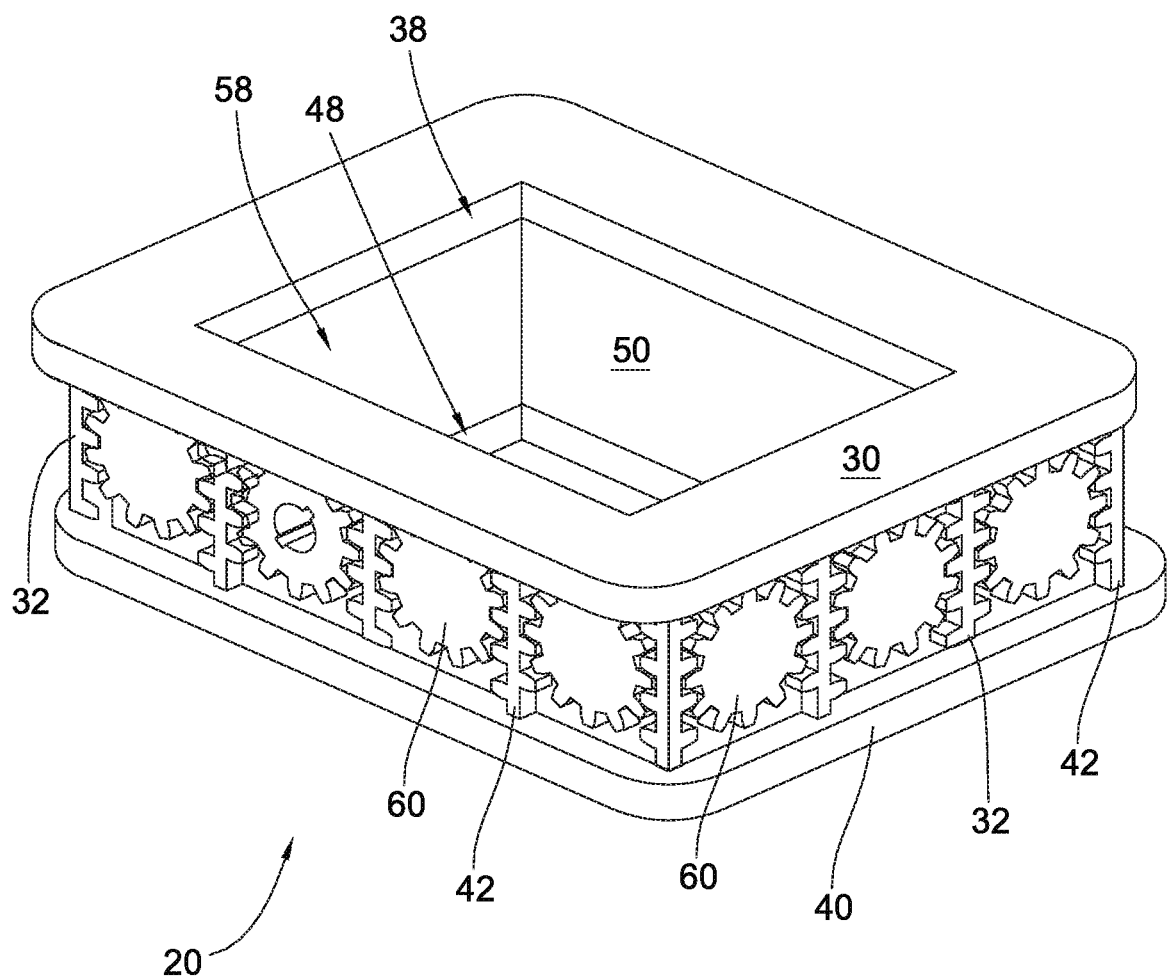
FIG. 1 is an isometric view of an expandable interbody device.

For the purposes of promoting an understanding of the principles of what is claimed, reference will now be made to embodiments illustrated in the drawings and specific language will be used to describe the same. It will nevertheless be understood that no limitation of the scope of the claims is thereby intended. Any alterations and further modifications in the illustrated device, and any further applications of the principles disclosed and illustrated herein are contemplated as would normally occur to one skilled in the art to which the disclosure relates.

With respect to the specification and claims, it should be noted that the singular forms "a", "an", "the", and the like include plural references unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

DEFINITION: "Engagement surface" as used herein, is directed to any known surface that can be used to engage a manual or automatic tool, including a cylindrical surface engageable by a one-way clutch or roller clutch, to permit rotation of gears. Engagement surface may include a geometric shape that is engageable by a corresponding geometric shape on a tool. Engagement surface may also encompass teeth on gears that are directly engaged by a tool.

There are currently two primary methods used to fuse bone with an interbody device: via a static spacer; or via an expandable interbody device. Static spacers is a structure that can hold an amount of bone graft material and maintain its shape when surgically inserted between two bones, for example, in a spinal fusion. The static spacer acts as a temporary strut to hold the space open while a solid bony fusion occurs. Static spacers come in fixed sizes and shapes.

Expandable interbody devices also act as a temporary strut to maintain the spacing between two bones, but they are adjustable in size after being positioned.

Generally, expandable interbody devices have an initial shape with a thin profile to permit initial positioning with a reduced sized opening in the patient's body. Once positioned, expandable interbody devices can be expanded in at least one dimension to increase the size of the expandable interbody device, and the resultant space between the two bones.

However, many expandable interbody devices provide little or no space for holding an amount of bone graft material. Many mechanism currently in use take up a significant portion of the volume of the expanding interbody device, leaving little or no room for graft material.

Disclosed below is an expandable interbody device that positions the expansion mechanisms in a peripheral wall of the device, leaving a large chamber in the middle of the device that can be filled with bone graft material, maximizing the area of bony fusion while fulfilling the requirements of a temporary strut while the bony fusion occurs.

While the disclosure below focuses on an expandable interbody device used for spinal fusion, it should be understood that the disclosed expansion mechanism could be used with other medical devices that require a three dimensional structure for stability (e.g., an intramedullary nail or joint replacement device).

Referring to FIG. 1, expandable interbody device 20 is illustrated. Expandable interbody device 20 generally includes plates 30 and 40 and support structure 50. Plates 30 and 40 include racks 32 and 42 that engage with gears 60. Rotation of gears 60 in an opening direction moves plates 30 and 40 away from support structure 50 due to the engagement of racks 32 and 42 with gears 60 as described below. Plate 30 defines chamber 38, plate 40 defines chamber 48, and support structure 50 defines chamber 58. Chambers 38, 48 and 58 are substantially aligned along a vertical axis of expandable interbody device 20 to define an area that bone graft material can be placed to provide bony fusion.

Interbody device 20 includes in expandable interbody device 20 to rotationally interlock all the gears 60 so that movement of one gear 60 moves all gears 60 substantially in unison. FIG. 1 includes positioning racks 32 and racks 42 on each outside corner. While not illustrated, other options for interlocking gears includes, but is not limited to, adding an additional gear or gears to each outside corner, positioning gears on adjacent walls so that the teeth on gears on adjacent walls interconnect, or any other known technique to interlock gears around an angle.

Figure 2:
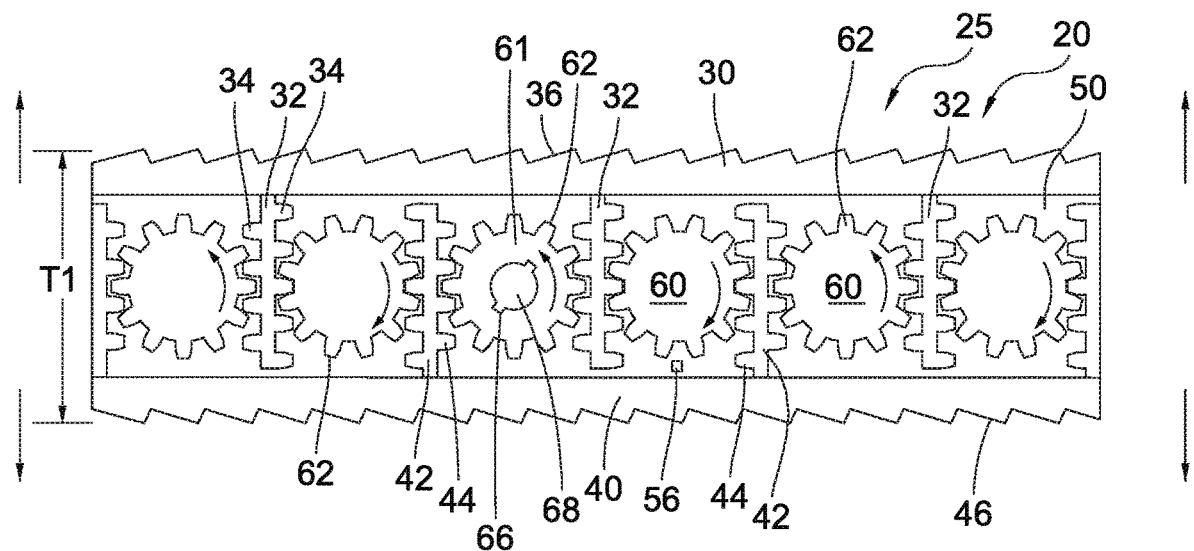
FIG. 2 is a front view of the expandable interbody device of FIG. 1 illustrating a first gearing layout in a minimum thickness configuration.

Referring now to FIG. 2, gear layout 25 is illustrated. FIG. 2 illustrates plate 30 which includes a plurality of racks 32, each rack 32 including a plurality of teeth 34. Plate 30 includes surface 36 which includes surface features to reduce or prevent migration of plate 30 relative to a bone after installation in a body. As shown in FIGS. 1 and 7-10, plate 30 defines chamber 38.

FIG. 2 also illustrates plate 40 which includes a plurality of racks 42, each rack 42 including a plurality of teeth 44. Plate 40 includes surface 46 which include surface features to reduce or prevent migration of plate 40 relative to a bone after installation in a body. As shown in FIGS. 1 and 7-10, plate 40 defines chamber 48.

FIG. 2 also illustrates a plurality of gears 60 that are positioned between alternating racks 32 and 42 with teeth 62 on gears 60 engaged with teeth 34 and 44 on racks 32 and 42. Gears 60 are rotationally coupled to support structure 50. Rotation of gears 60 in the opening direction, shown by arrows, moves plates 30 and 40 away from support structure 50.

As shown in FIG. 2, racks 32 and 42 are positioned directly between adjacent gears 60 such that, if racks 32 and 42 were removed, gears 60 would not interact with each other. Gears 60 with racks 32 and 42 are arranged around the entire periphery support structure 50 (which extends between plates 30 and 40). Rotation of one gear 60 moves all racks 32 and 42 and all gears 60 together in unison. FIG. 2 shows gear layout 25 with plates 30 and 40 spaced apart a minimum extension T1.

Gear layout 25 also includes locking mechanism 56. Locking mechanism 56 is movable relative to support structure 50 and gears 60. Locking mechanism 56 can be moved, for example, by a tool, to engage teeth 62 on a gear 60 to block rotation of gear 60.

Also shown in FIG. 2 is gear 61 that is rotationally coupled to support structure 50. Gear 61 includes engagement surface 66 and window 68. Engagement surface 66 permits the rotation of gear 61 (and all interconnected gears 60 and racks 32 and 34) with a tool with corresponding surfaces to interface with engagement surface 66 operated by a surgeon. Window 68 extends through gear 61 and support structure 50 permitting passage of bone graft material through support structure 50. The tool that engages engagement surface 66 may optionally include a lumen to pass bone graft material.

Figure 3:
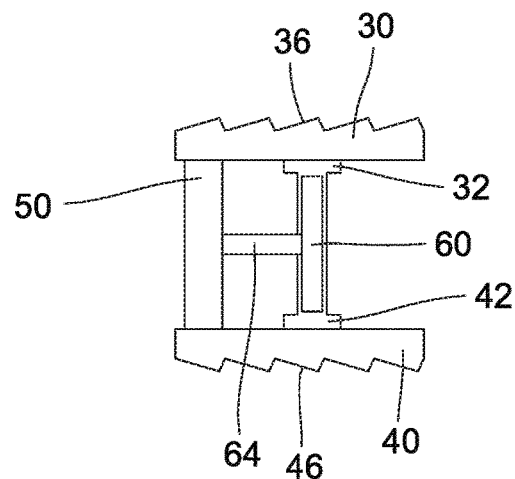
FIG. 3 is a side view of the FIG. 2 first gearing layout.

Referring now to FIG. 3, a side view of the arrangement shown in FIG. 2 is illustrated. FIG. 3 shows support structure 50 and rotatable connection 64 that rotatably connects gears 60 with support structure 50. FIG. 3 also illustrates plate 30 with rack 32 and surface 26 and plate 40 with rack 42 and surface 46. Racks 32 and 42 are engaged with gears 60 as described above.

Figure 4:
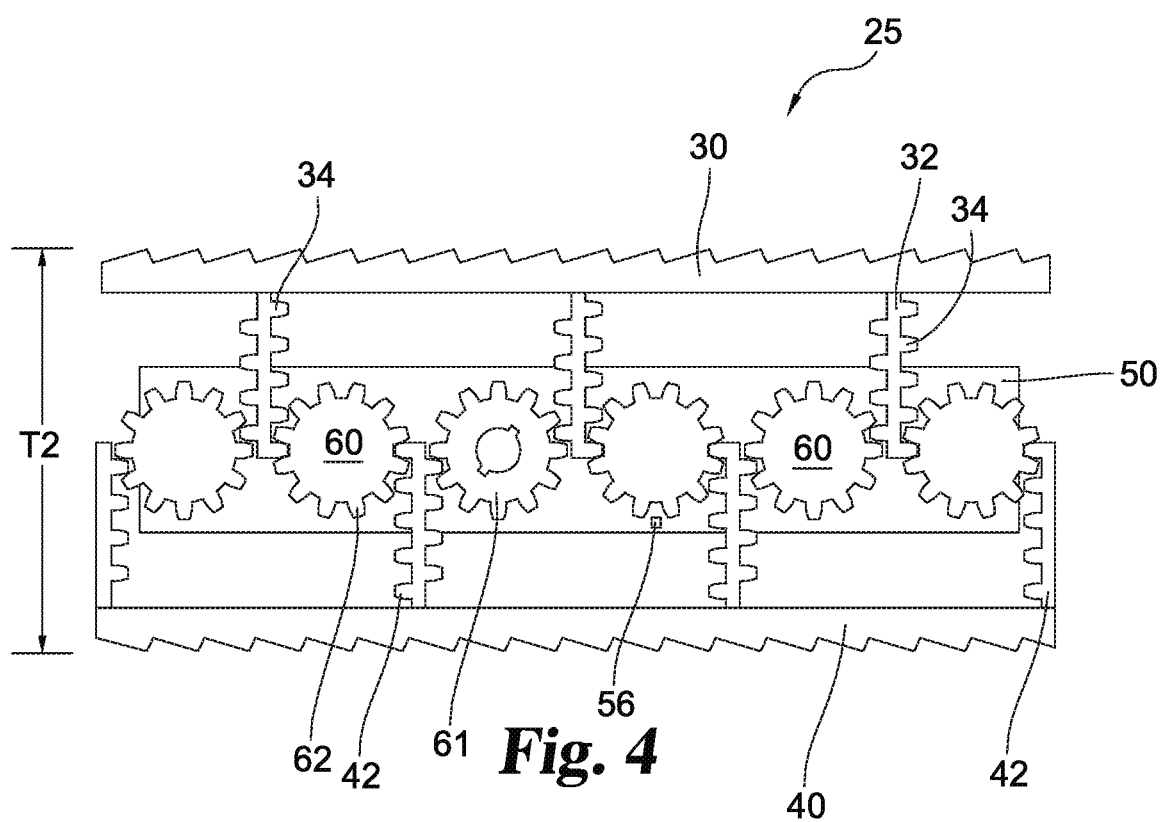
FIG. 4 is a front view of the FIG. 2 first gearing layout in a maximum thickness configuration.

Referring now to FIG. 4, gear layout 25 is illustrated in an expanded condition with gears 60 rotated in the opening direction with plates 30 and 40 spaced apart a maximum extension T2. T2 may be at least 150% of T1.

Figure 5:
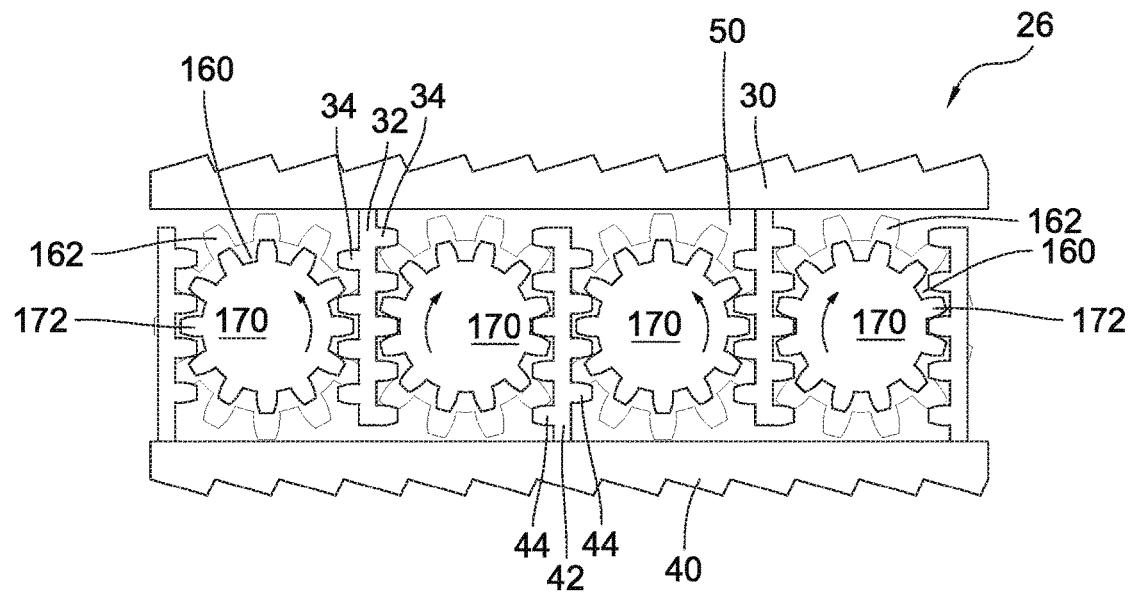
FIG. 5 is a front view of an expandable interbody device illustrating a second gearing layout in a minimum thickness configuration.

Referring to FIG. 5, gear layout 26 is illustrated. FIG. 5 illustrates plate 30 which includes a plurality of racks 32, each rack 32 including a plurality of teeth 34. FIG. 5 also illustrates plate 40 which includes a plurality of racks 42, each rack 42 including a plurality of teeth 44.

FIG. 5 also illustrates a plurality of gears 160 and a plurality of gears 170 that rotate with gears 160. Gears 170 are positioned between alternating racks 32 and 42 with teeth 172 on gears 170 engaged with teeth 34 and 44 on racks 32 and 42. Gears 160 are interlocked with the teeth on adjacent gears 160 such that teeth 162 are interlocked so that rotation of one gear 160 rotates adjacent gears 160. Gears 160 and 170 are rotationally coupled to support structure 50. Rotation of gears 160 and 170 in the opening direction, shown by arrows, moves plates 30 and 40 away from support structure 50.

Figure 6:
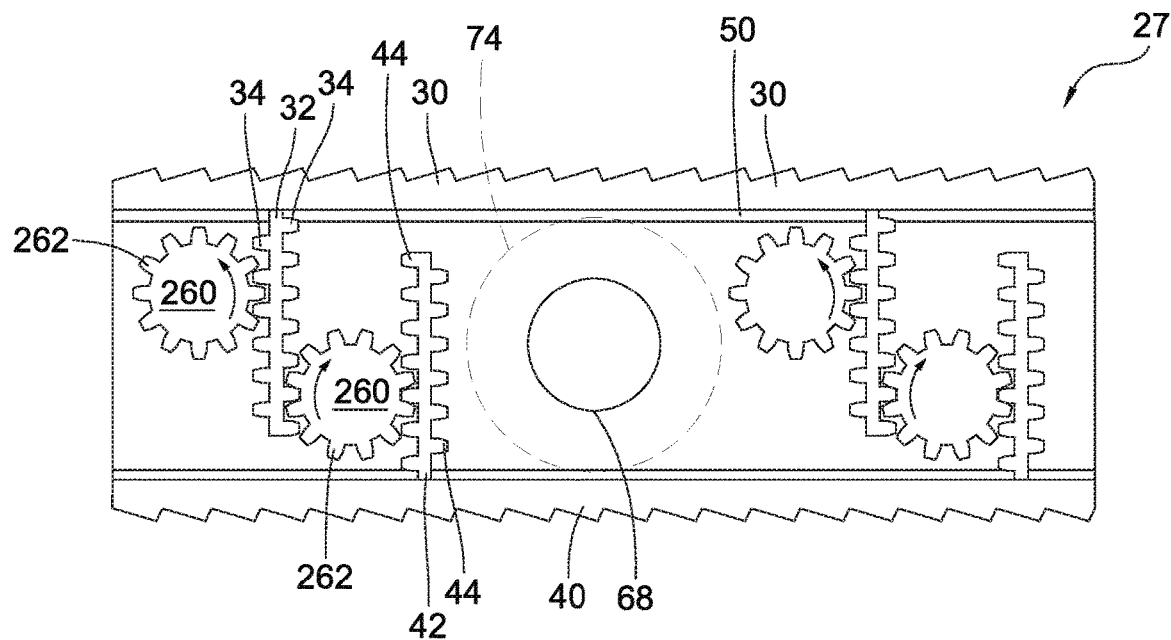
FIG. 6 is a front view of an expandable interbody device illustrating a third gearing layout in a minimum thickness configuration.

Referring to FIG. 6, gear layout 27 is illustrated. FIG. 6 illustrates plate 30 which includes a plurality of racks 32, each rack 32 including a plurality of teeth 34. FIG. 6 also illustrates plate 40 which includes a plurality of racks 42, each rack 42 including a plurality of teeth 44.

FIG. 6 also shows a plurality of gears 260 that each includes a plurality of teeth 262. Gears 260 are positioned between alternating racks 32 and 42 with teeth 262 on gears 260 engaged with teeth 34 and 44 on racks 32 and 42. Gears 260 are rotationally coupled to support structure 50. Rotation of gears 260 in the opening direction, shown by arrows, moves plates 30 and 40 away from support structure 50.

As shown in FIG. 6, racks 32 and 42 are positioned directly between adjacent gears 260 such that, if racks 32 and 42 were removed, gears 260 would not interact with each other. Gears 260 with racks 32 and 42 may be arranged around the entire periphery support structure 50 (which extends between plates 30 and 40). Rotation of one gear 260 moves all racks 32 and 42 and all gears 260 together in unison.

Also as shown in FIG. 6, gear layout 27 includes open space 74 between an adjacent rack 40 and a gear 260. Open space 74 may optionally be used to provide a location for an external tool to interface with gears 260 to rotate gears 260 to move racks 30 and 40. Such a tool could have a tooth pattern that would interlock with the teeth on gears 260 and rack 40.

FIG. 6 also shows gear layout 27 with window 68 in support structure 50. Window 68 extends through support structure 50 permitting passage of bone graft material through support structure 50. The tool that engages gears 260 may optionally include a lumen to pass bone graft material.

Figure 7:
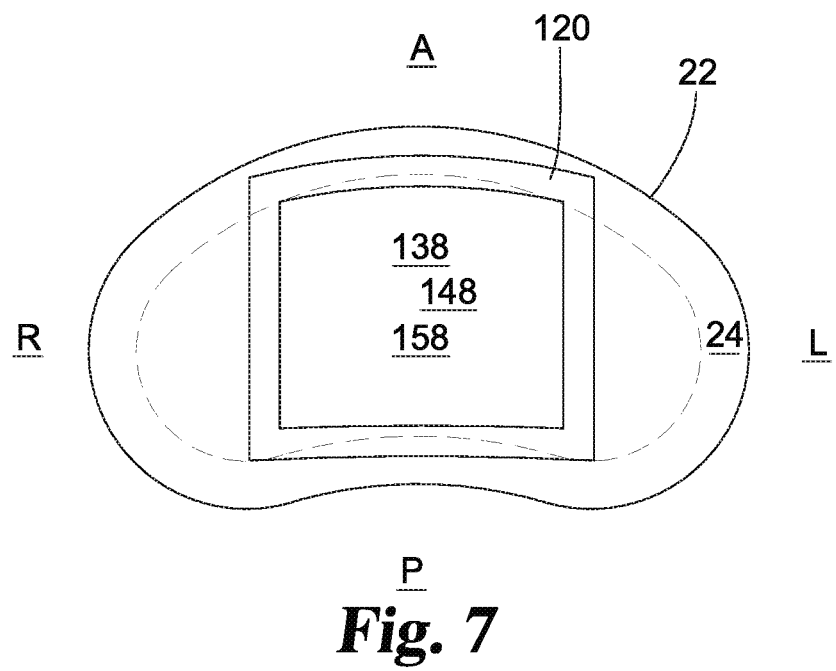
FIG. 7 is a top plan view of a second expandable interbody device juxtaposed over a representative vertebral body.
Figure 8:
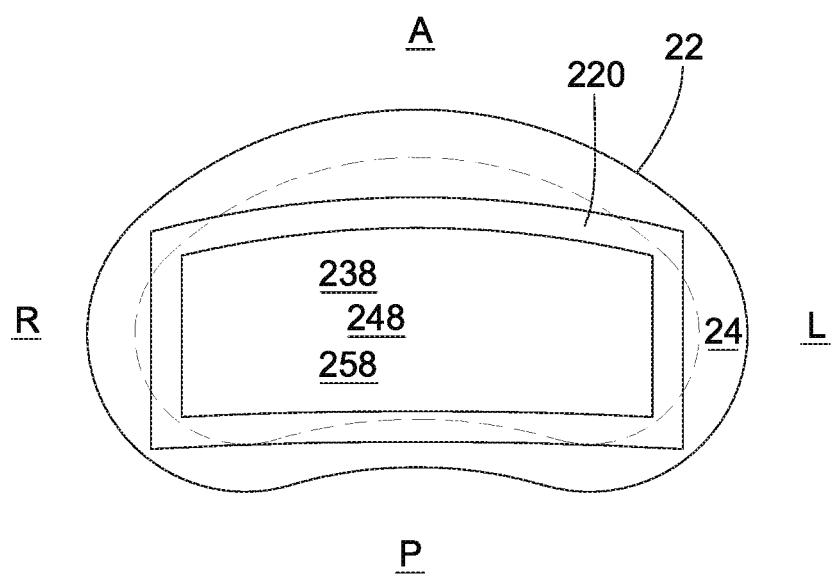
FIG. 8 is a top plan view of a third expandable interbody device juxtaposed over a representative vertebral body.
Figure 9:
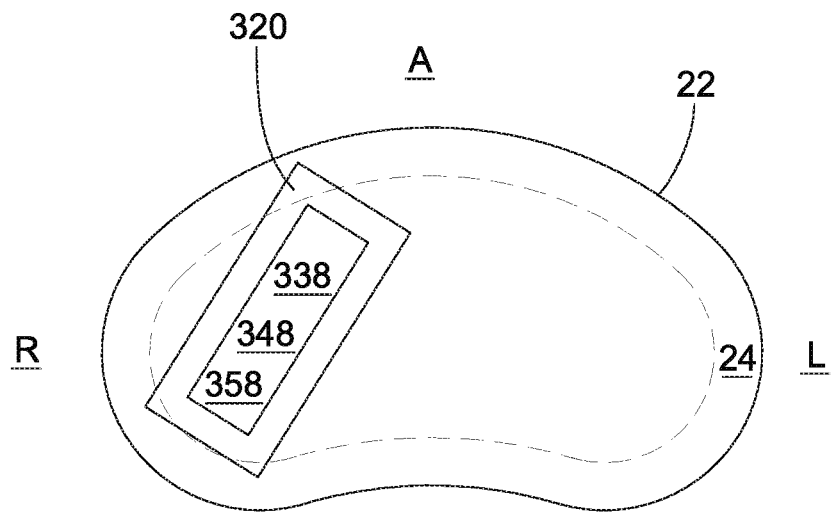
FIG. 9 is a top plan view of a fourth expandable interbody device juxtaposed over a representative vertebral body.
Figure 10:
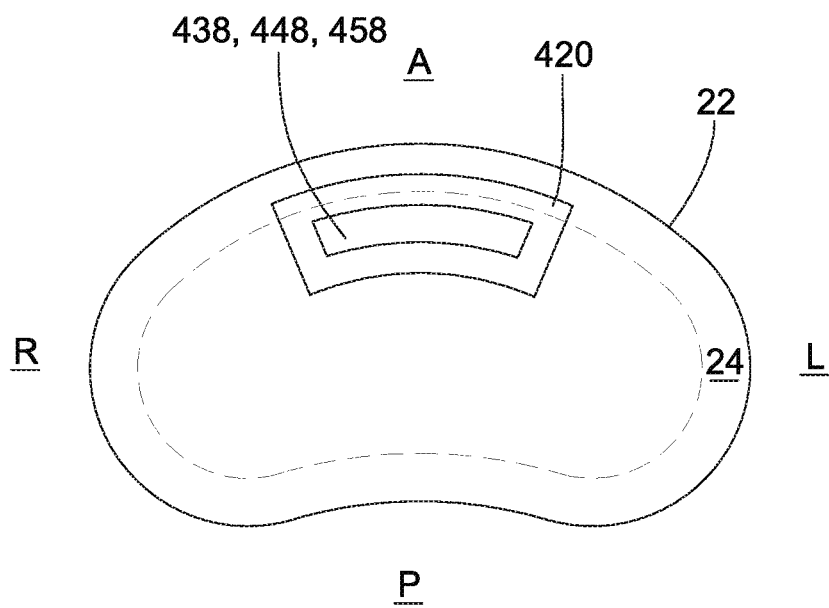
FIG. 10 is a top plan view of a fifth expandable interbody device juxtaposed over a representative vertebral body.

Referring now to FIGS. 7-10, Expandable interbody devices 120, 220, 320 and 420 are illustrated juxtaposed over a representative vertebral body 22 in a top down view. Vertebral body 22 includes aposphyseal ring 24. For reference, each drawing of vertebral body 22 is marked with anterior side A, posterior side P, right side R and left side L. Expandable interbody devices 120, 220, 320 and 420 each have a different shape to facilitate spinal fusion using different access routes. FIG. 7 demonstrates an interbody shape that would be typical for use in an anterior approach through the retroperitoneal space for an anterior lumbar interbody fusion. Insertion would occur from anterior side A. FIG. 8 demonstrates an interbody shape used in a lateral interbody fusion via either a direct lateral approach or anterolateral approach through the retroperitoneal space. Insertion in these would occur from either right side R or left side L. Both FIG. 9 and FIG. 10 demonstrate an interbody device shape typically used in a posterior approach such as for a transforaminal lumbar interbody fusion or a posterior lumbar interbody fusion. Insertion in these occur either in an oblique or perpendicular fashion to posterior side P. In each case, at least a portion of the expandable interbody device is positioned between aposphyseal rings on adjacent vertebra.

Figure 11:
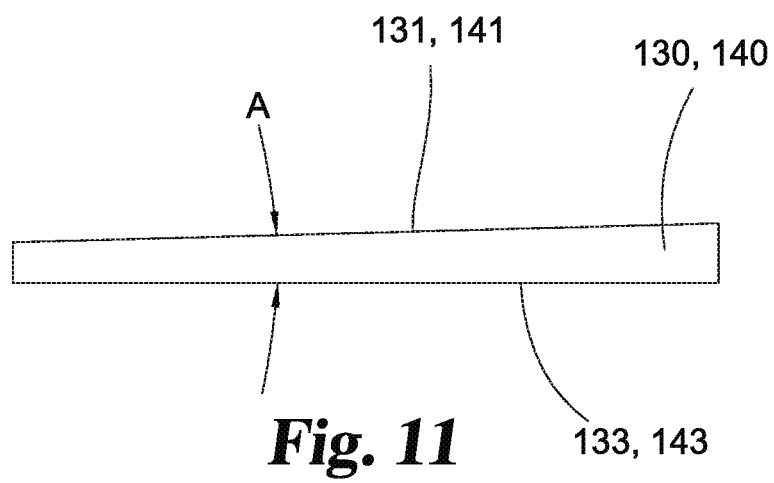
FIG. 11 is a front view of an alternative embodiment of a plate, a component of the FIG. 1 expandable interbody device.

Referring now to FIG. 11, plate 130, 140 is illustrated. Plate 130, 140 includes a sloped thickness. Plate 130, 140 includes surface 131, 141 and surface 133, 143 that are angled related to each other by angle A. Plates 130, 140 may be used instead of plates 30 and 40 to provide an angle to a particular expandable interbody device that can be used to configure the expandable interbody device to a particular patient's anatomy, including lordotic angle for a particular fusion. Different plates 130, 140 may be provided with different angles A. For example, different plates 130, 140 could be selected from standard sizes with angle A equal to 3°, 6° or 9°. Or any other angle A could be provided.

Expandable interbody devices 20, 120, 320 and 420 may also use different gear layouts on different sides of a particular expandable interbody device. For example, gear layout 25 could be used on one side of the devise and gear layout 26 could be used on an opposite side of the device to create an asymmetrical expansion such that one side moves more than the other side when gears are rotated, again to configure the expandable interbody device to a particular patient's anatomy, including lordotic angle for a particular fusion. Asymmetrical expansion could also be used in combination with angled plates or could be used with flat plates.

Figure 12:
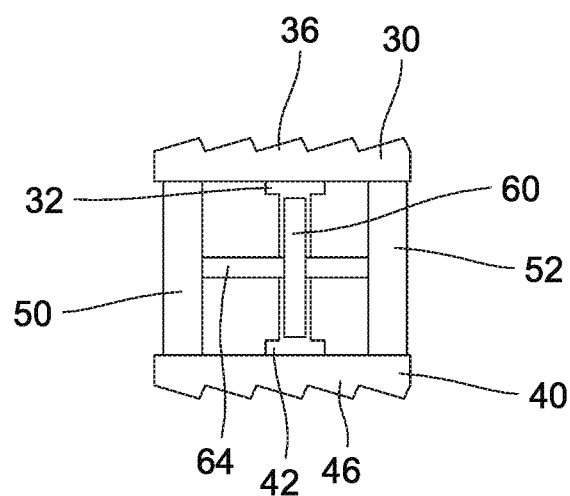
FIG. 12 is an alternative embodiment of the FIG. 3 side view of the FIG. 2 first gearing layout.

Referring now to FIG. 12, an alternative embodiment of the arrangement shown in FIG. 3 is illustrated. FIG. 12 shows support structure 50, support structure 52, and rotatable connection 64 that rotatably connects gears 60 with support structures 50 and 52. FIG. 12 also illustrates plate 30 with rack 32 and surface 26 and plate 40 with rack 42 and surface 46. Racks 32 and 42 are engaged with gears 60 as described above.

Figure 13:
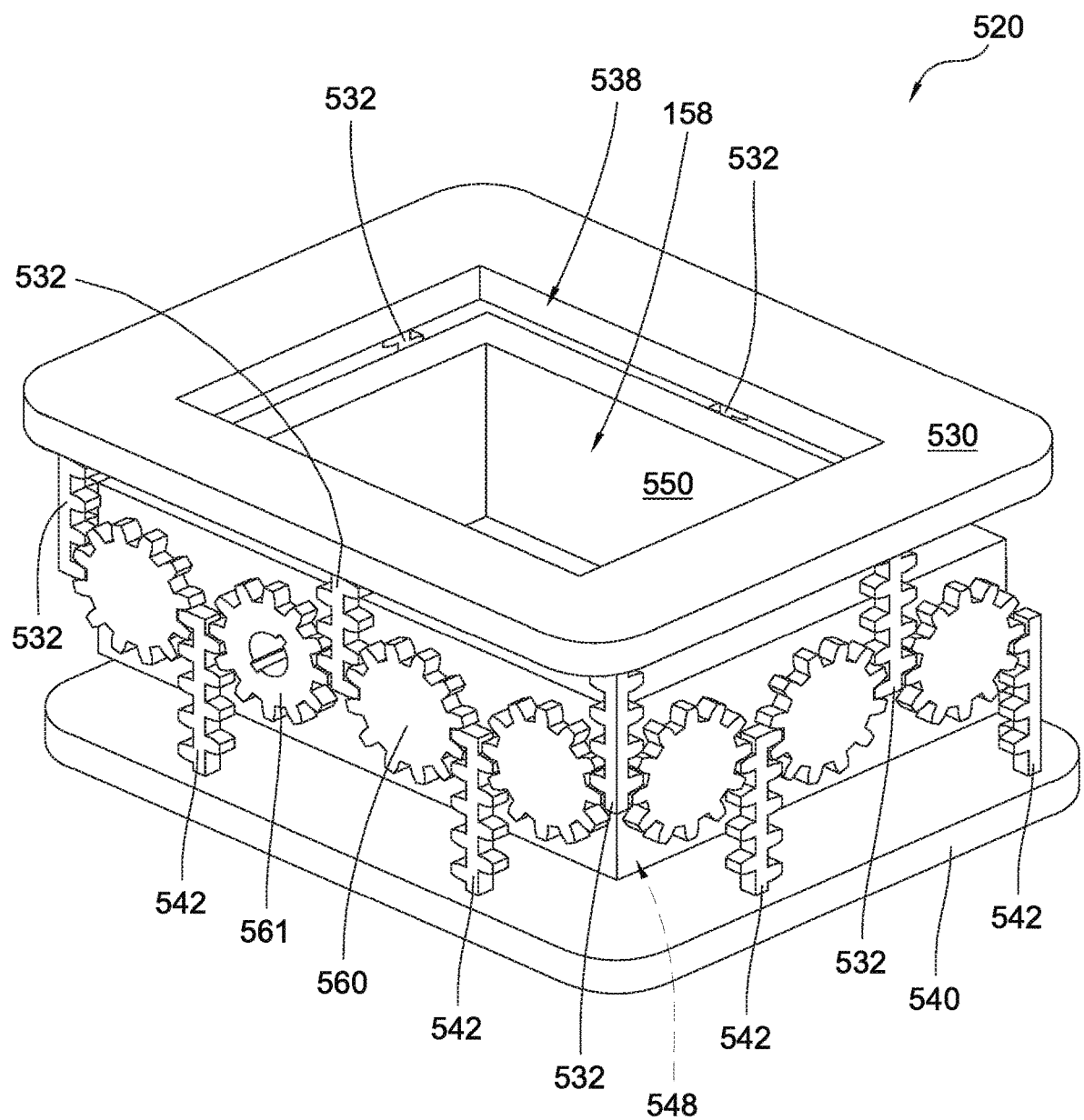
FIG. 13 is an isometric view of an alternative embodiment of an expandable interbody device.

Referring to FIG. 13, expandable interbody device 520 is illustrated. Expandable interbody device 520 generally includes plates 530 and 540 and support structure 550. Plates 530 and 540 include racks 532 and 542 that engage with gears 560. Rotation of gears 560 in an opening direction moves plates 530 and 540 away from support structure 550 due to the engagement of racks 532 and 542 with gears 560 as described below. Plate 530 defines chamber 538, plate 540 defines chamber 548, and support structure 550 defines chamber 558. Chambers 538, 548 and 558 are substantially aligned along a vertical axis of expandable interbody device 520 to define an area that bone graft material can be placed to provide bony fusion.

FIG. 13 illustrates interbody device 520 in an expanded condition with plates 530 and 540 spaced apart at near the maximum possible displacement.

Figure 14:
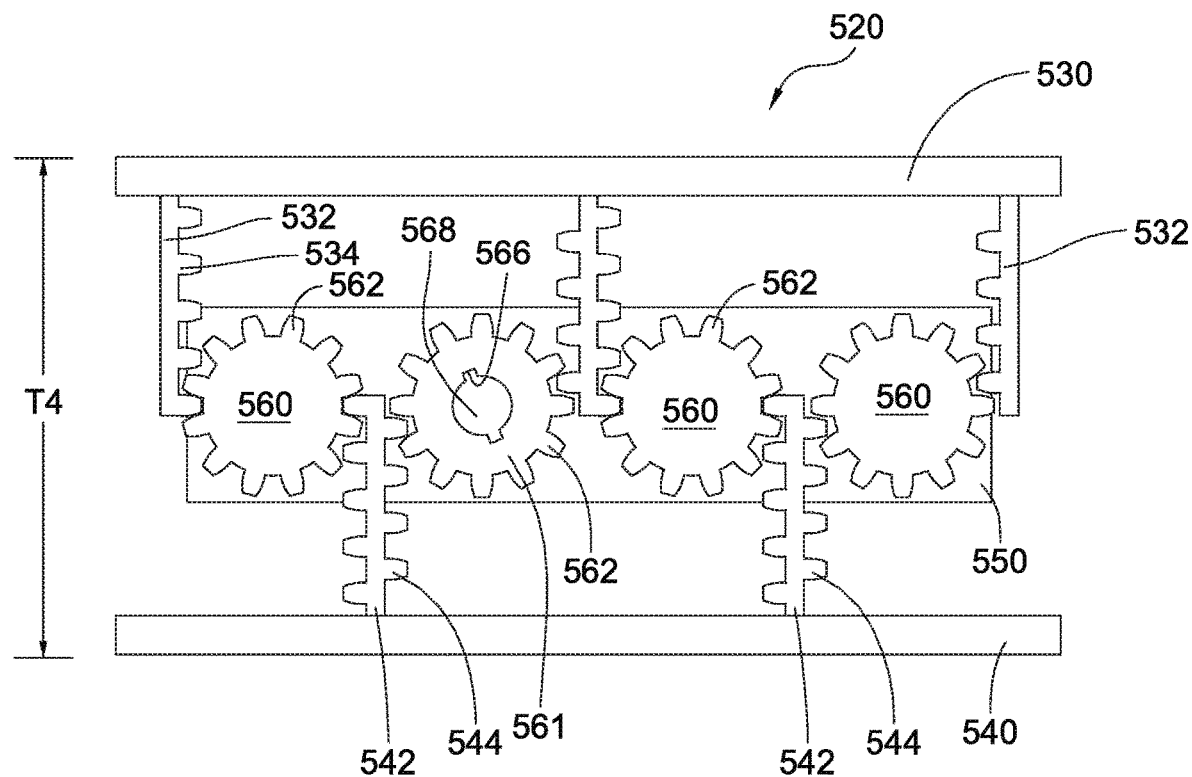
FIG. 14 is a side view of the FIG. 13 expandable interbody device.

Referring now to FIG. 14, a side view of interbody device 520 is illustrated. Interbody device 520 includes plate 530 which includes a plurality of racks 532, each rack 532 including a plurality of teeth 534. Plate 530 may include surface features to reduce or prevent migration of plate 530 relative to a bone after installation in a body. Interbody device 520 also illustrates plate 540 which includes a plurality of racks 542, each rack 542 including a plurality of teeth 544. Plate 540 may include surface features to reduce or prevent migration of plate 540 relative to a bone after installation in a body. Interbody device 520 also includes a plurality of gears 560 that are positioned between alternating racks 532 and 542 with teeth 562 on gears 560 engaged with teeth 534 and 544 on racks 532 and 542. Gears 560 are rotationally coupled to support structure 550. FIG. 14 illustrates gears 560 rotated in the opening direction with plates 530 and 540 moved away from support structure 550 with plates 530 and 540 spaced apart a maximum extension T4.

As shown in FIG. 14, racks 532 and 542 are positioned directly between adjacent gears 560 such that, if racks 532 and 542 were removed, gears 560 would not interact with each other. Gears 560 with racks 532 and 542 are arranged around the entire periphery support structure 550 (which extends between plates 530 and 540). Rotation of one gear 560 moves all racks 532 and 542 and all gears 560 together in unison.

Figure 15:
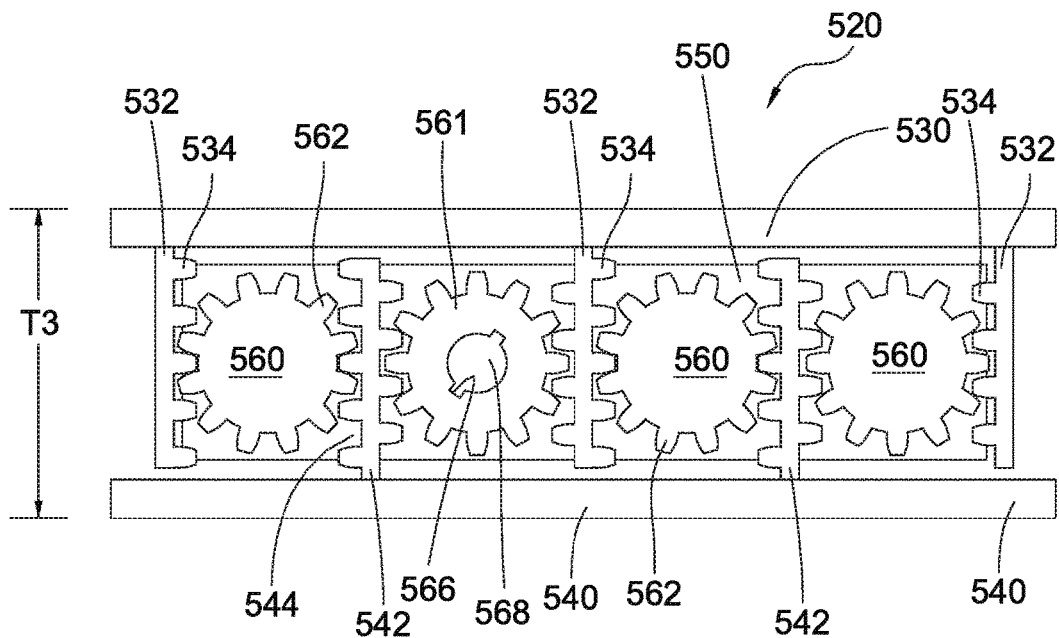
FIG. 15 is a side view of the FIG. 13 expandable interbody device in a retracted position.

Referring now to FIG. 15, a side view of interbody device 520 is illustrated in a retracted condition with gears 560 rotated opposite the opening direction with plates 530 and 540 spaced apart a minimum extension T3. T4 may be at least 150% of T3.

Figure 16:
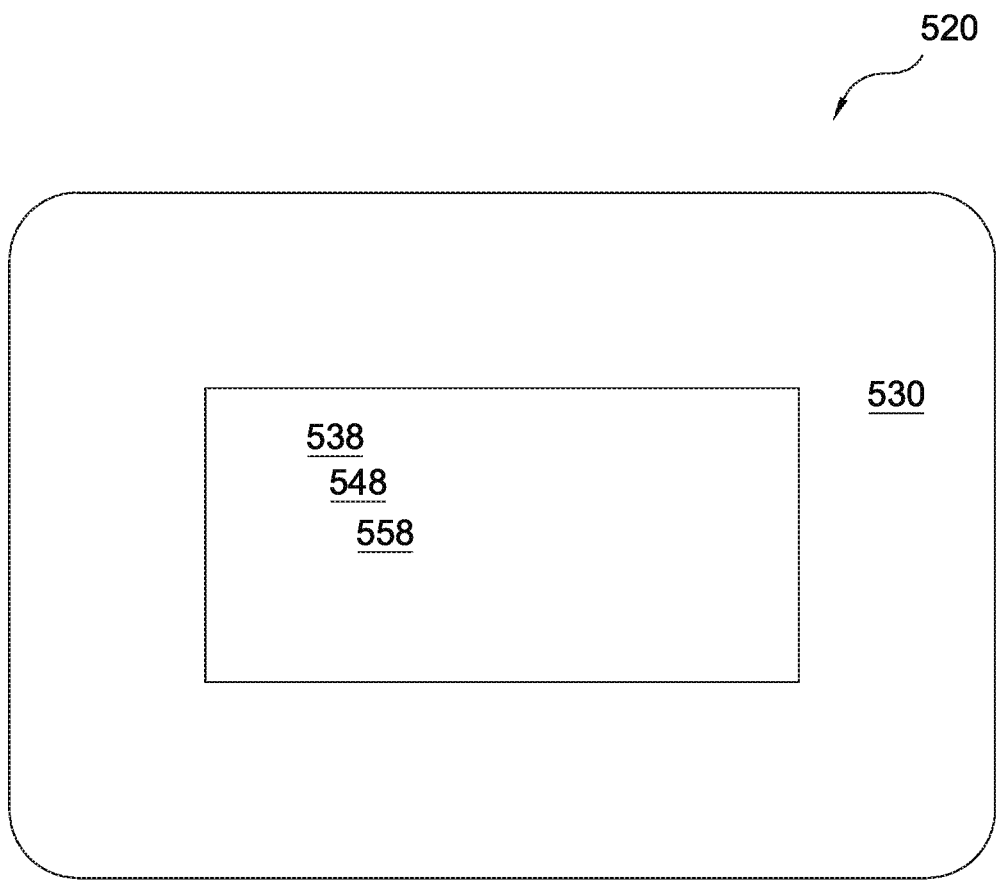
FIG. 16 is a top view of the FIG. 16 expandable interbody device.

Referring now to FIG. 16, a top view of interbody device 520 shows plate 530 and chambers 538, 548 and 558.

Figure 17:
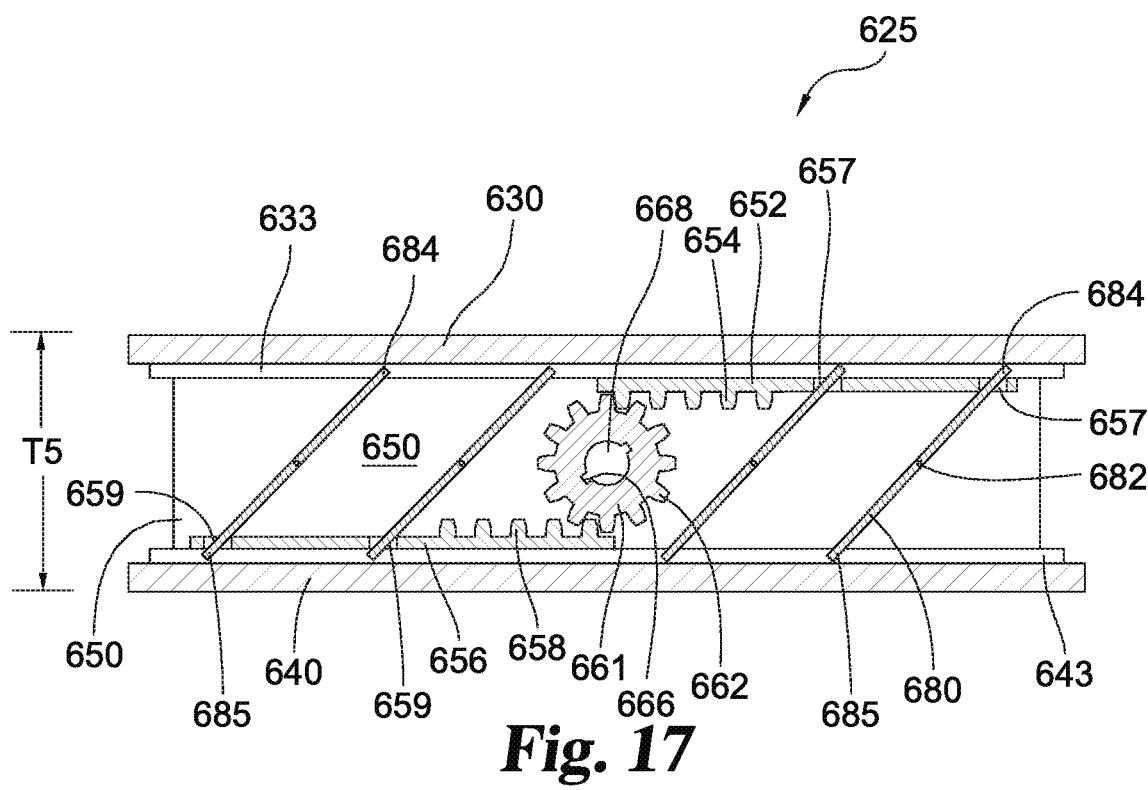
FIG. 17 is a side cross-sectional view of an alternative embodiment of a gearing layout in a retracted position.

Referring to FIG. 17, gear layout 625 is illustrated. Gear layout 625 includes plate 630, plate 640, support structure 650, rack 652, rack 656, gear 661 and rods 680. Plate 630 defines groove 633 that retains ends 684 of rods 680. Plate 640 defines groove 643 that retains ends 685 of rods 680 to move only in a linear direction. Rack 652 includes a plurality of teeth 654 that engage with teeth 662 on gear 661. Rack 652 defines a plurality of recesses 657 that retain rods 680 to move only in a linear direction. Rack 656 includes a plurality of teeth 658 that engage with teeth 662 on gear 661. Rack 656 defines a plurality of recesses 659 that retain rods 680.

Rods 680 are pivotally coupled to support structure 650 at pivot points 682. Rotation of gear 661 moves racks 652 and 656 in opposite directions. Rods 680 are engaged with racks 652 and 656 via recesses 657 and 659 so that ends 684 and 685 move with racks 652 and 656. FIG. 17 illustrates gear layout in a retracted configuration with plates 630 and 640 spaced apparat a minimum extension T5.

Gear 661 includes engagement surface 666 and window 668. Engagement surface 666 permits the rotation of gear 661 with a tool with corresponding surfaces to interface with engagement surface 666 operated by a surgeon. Window 668 extends through gear 661 and support structure 650 permitting passage of bone graft material through support structure 650. The tool that engages engagement surface 666 may optionally include a lumen to pass bone graft material.

Figure 18:
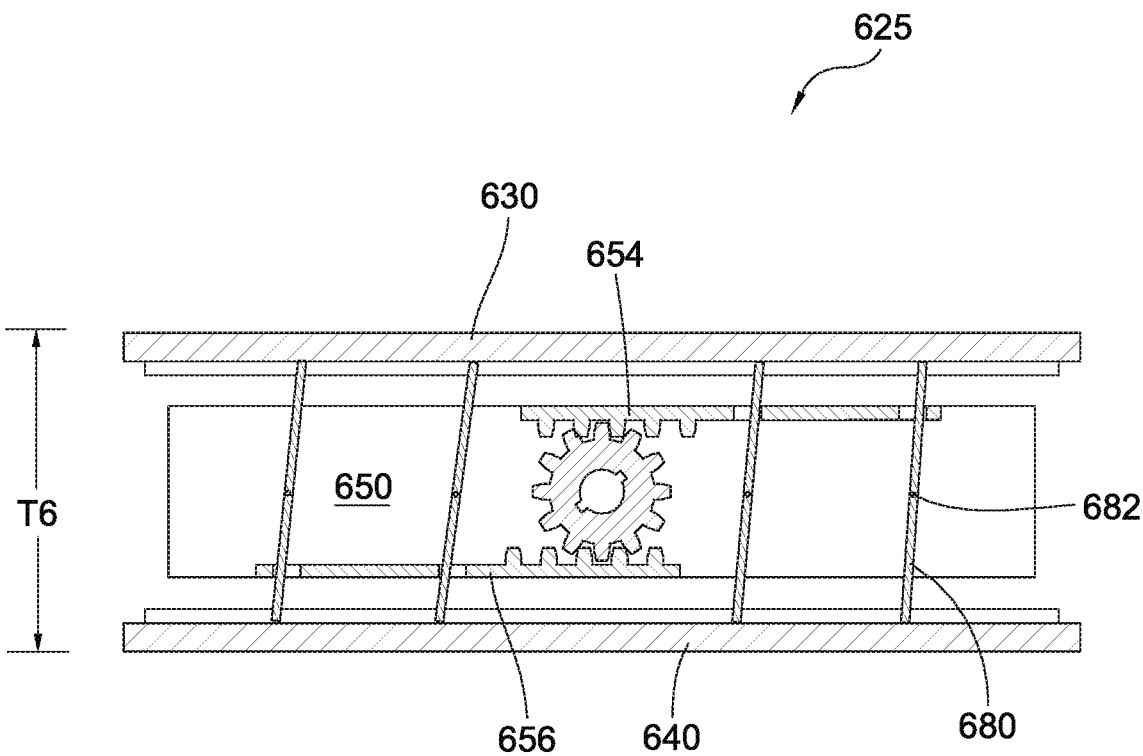
FIG. 18 is a side cross-sectional view of the FIG. 17 gearing layout in an expanded position.

Referring to FIG. 18, gear layout 625 is illustrated in an expanded configuration with rods 680 moved to nearly vertical orientations and plates 630 and 640 spaced apart a maximum extension T6.

Figure 19:
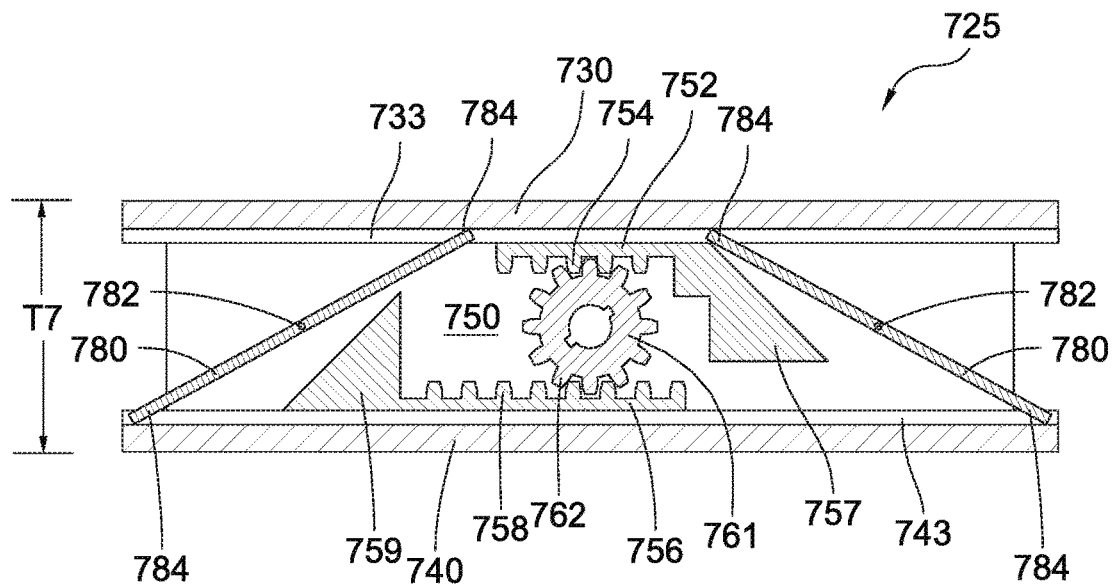
FIG. 19 is a side cross-sectional view of an alternative embodiment of a gearing layout in a retracted position.

Referring to FIG. 19, gear layout 725 is illustrated. Gear layout 725 includes plate 730, plate 740, support structure 750, rack 752, rack 756, gear 761 and rods 780. Plate 730 defines groove 733 that retains ends 784 of rods 780. Plate 740 defines groove 743 that retains ends 785 of rods 780 to move only in a linear direction. Rack 752 includes a plurality of teeth 754 that engage with teeth 762 on gear 761. Rack 752 includes abutment 757 that abuts rod 780. Rack 756 includes a plurality of teeth 758 that engage with teeth 762 on gear 761. Rack 756 includes abutment 759 that abuts rod 780.

Rods 780 are pivotally coupled to support structure 750 at pivot points 782. Rotation of gear 761 moves racks 752 and 756 in opposite directions. Abutments 757 and 759 push against rods 780 and determine the relative angle of rods 780. FIG. 19 illustrates gear layout 725 in a retracted configuration with plates 730 and 740 spaced apparat a minimum extension T7.

Gear 761 includes engagement surface 766 and window 768. Engagement surface 766 permits the rotation of gear 761 with a tool with corresponding surfaces to interface with engagement surface 766 operated by a surgeon. Window 768 extends through gear 761 and support structure 750 permitting passage of bone graft material through support structure 750. The tool that engages engagement surface 766 may optionally include a lumen to pass bone graft material.

Figure 20:
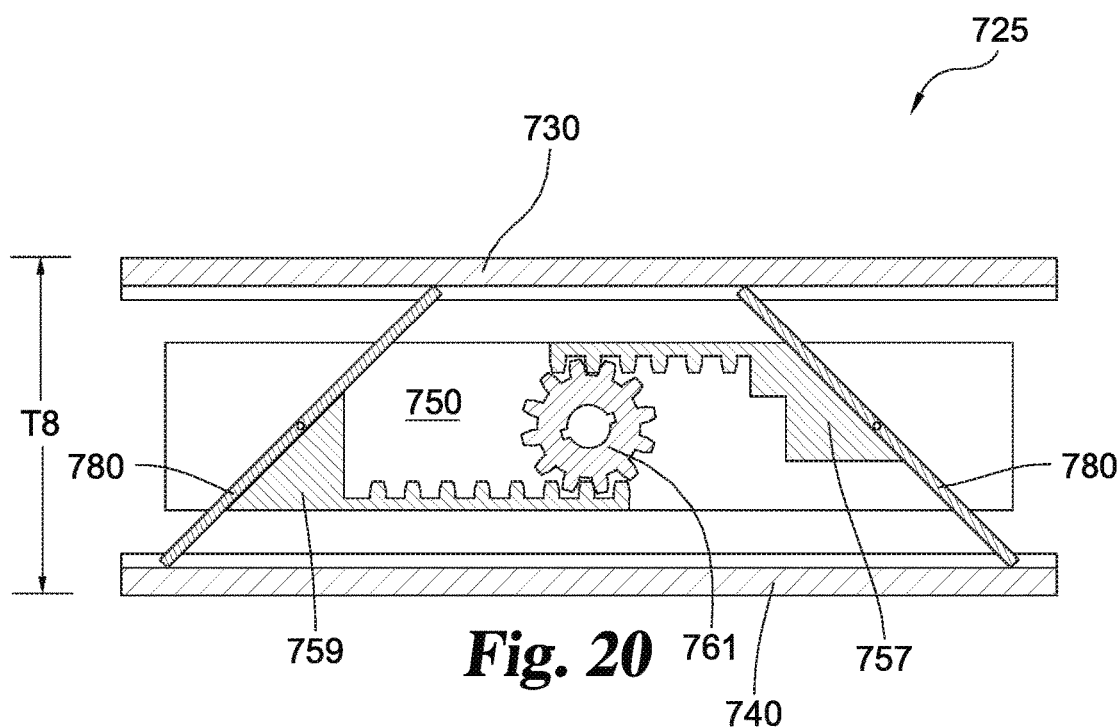
FIG. 20 is a side cross-sectional view of the FIG. 19 gearing layout in an expanded position.

Referring to FIG. 20, gear layout 725 is illustrated in an expanded configuration with rods 780 moved to abut along the length of abutment surfaces 757 and 759 with plates 730 and 740 spaced apart a maximum extension T8.

Note that while FIGS. 19 and 20 illustrate a single pair of abutment surfaces 757 and 759 and rods 780, any number of abutment surface and rods can be used. Additional abutment surfaces can be linearly connected to and spaced apart from racks 752 and 756 to move in unison with racks 752 and 756 against additional rods that are rotationally coupled to support structure 750.

Figure 21:
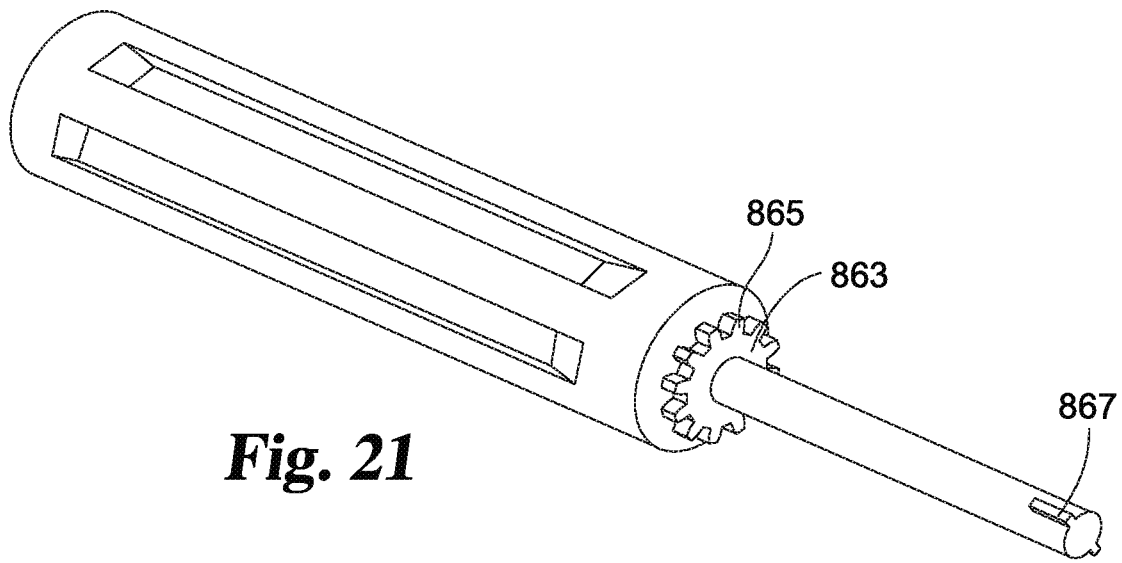
FIG. 21 is an isometric view of a tool.

Referring now to FIG. 21, tool 810 is illustrated. Tool 810 includes handle 812, gear 863 and engagement surfaces 867. Gear 865 includes a plurality of teeth 865 configured to engage with teeth such as on the devices disclosed above. Engagement surface 867 is configured to engage with engagement surfaces such as engagement surfaces 66, 566, 666, and 766. Tool 810 may be configured such that gear 865 and engagement surface 867 rotate together or independently.

Figure 22:
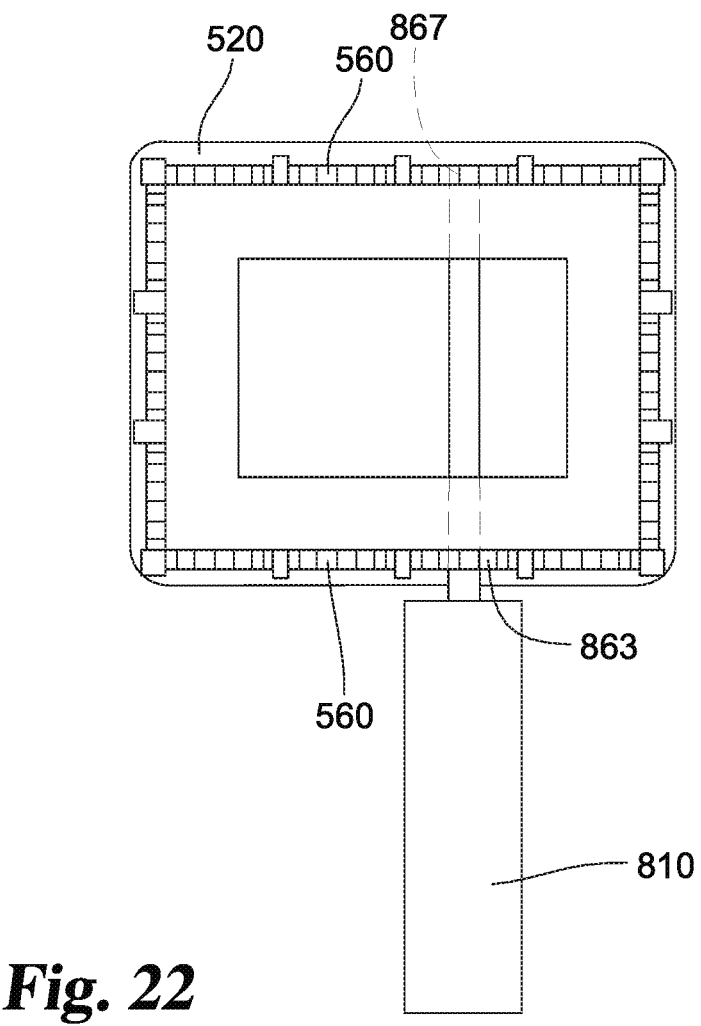
FIG. 22 is a top view of an expandable interbody device showing engagement of the FIG. 21 tool.

Referring now to FIG. 22, a top view of a modified expandable interbody device 520 is illustrated with tool 810. Device 520 is modified to create an open space that is filled with gear 865 while engagement surface 867 is engaged with engagement surface 566. In this embodiment, gear 865 and engagement surface 867 rotate in opposite directions.

Figure 23:
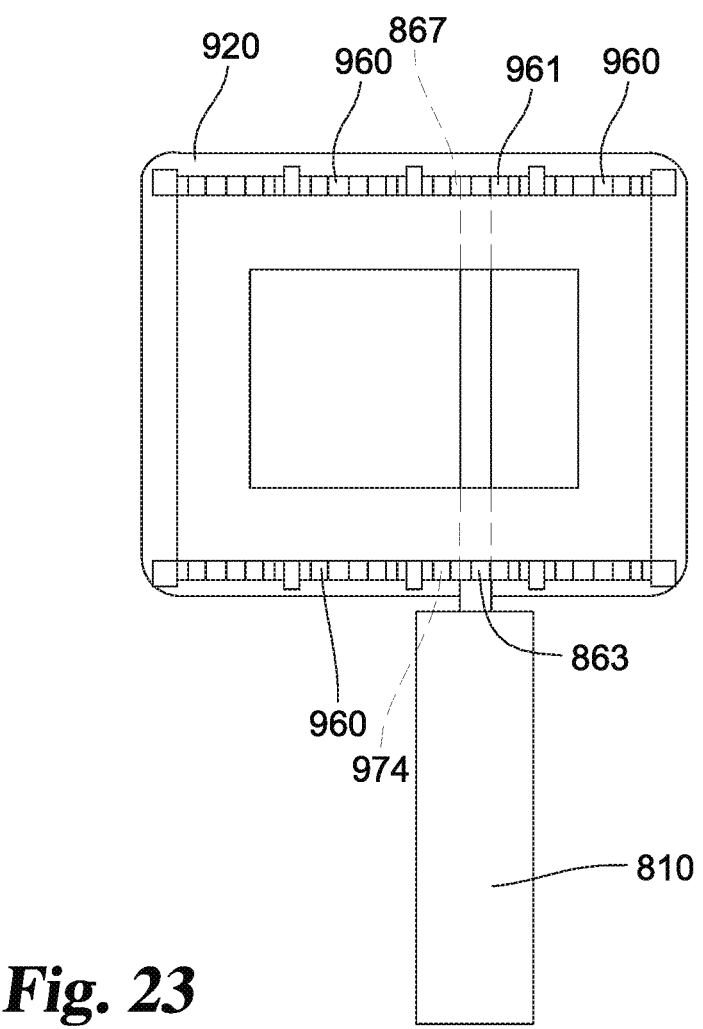
FIG. 23 is a top view of an alternative embodiment of an expandable interbody device showing engagement of the FIG. 21 tool.

Referring now to FIG. 23, a top view of expandable interbody device 920 is shown with tool 810. Device 920 includes two separate rows of gears and racks, similar to the gear layouts disclosed above. One row includes an open space 974 configured to receive gear 865 while the other row includes gear 961 that receives engagement surface 867 so that engagement surface 867 can rotate gear 961. Tool 810 may be configures such that gear 865 and engagement surface 867 rotate together to provide uniform expansion or tool 810 may be configured such that gear 865 and engagement surface 867 rotate independently to provide the capacity to adjust lordotic angle for a particular fusion.

While the claimed subject matter has been illustrated and described in detail in the drawings and foregoing description, the same is to be considered as illustrative and not restrictive in character. All changes and modifications that come within the spirit of the disclosure are desired to be protected by the claims.

I claim:

1. An expandable interbody device comprising:
   a support structure having a top side and a bottom side;
   a top plate positioned on the top side of the support structure;
   a bottom plate positioned on the bottom side of the support structure;
   a plurality of gears rotatably connected to the support structure, wherein the plurality of gears are rotatable relative to the support structure and wherein the plurality of gears are arranged such that adjacent gears are rotationally interconnected;
   a plurality of first racks that are coupled to the top plate, wherein the plurality of first racks are operationally connected to the plurality of gears such that rotating the plurality of gears in an opening direction moves the top plate away from the support structure by moving the plurality of first racks relative to the plurality of gears; and
   a plurality of second racks that are coupled to the bottom plate, wherein the plurality of second racks are operationally connected to the plurality of gears such that rotating the plurality of gears in an opening direction moves the bottom plate away from the support structure by moving the plurality of second racks relative to the plurality of gears.

2. The expandable interbody device of claim 1, wherein the support structure defines a first chamber that extends through the support structure.

3. The expandable interbody device of claim 2, further comprising a window that extends through the support structure and is adapted to pass graft material through the support structure to the first chamber.

4. The expandable interbody device of claim 2, wherein the top plate defines a second chamber that extends through the top plate.

5. The expandable interbody device of claim 4, wherein the bottom plate defines a third chamber that extends through the bottom plate.

6. The expandable interbody device of claim 5, wherein the first, second and third chambers are substantially aligned along a vertical axis of the expandable interbody device.

7. The expandable interbody device of claim 1, wherein the plurality of first and second racks are positioned between and interconnect adjacent gears of the plurality of gears.

8. The expandable interbody device of claim 1, wherein the plurality of gears each comprises a first set of gear teeth and a second set of gear teeth, wherein the first set of gear teeth interconnect with adjacent gears of the plurality of gears and wherein the second set of gear teeth are operationally connected to racks of the plurality of first and second racks.

9. The expandable interbody device of claim 1, further comprising an engagement surface that is arranged to engage with a tool to rotate the plurality of gears.

10. The expandable interbody device of claim 1, wherein the top plate defines a wedge shape.

11. The expandable interbody device of claim 10, wherein the bottom plate defines a wedge shape.

12. The expandable interbody device of claim 1, wherein the support structure includes a first side and a second side, wherein the first and second sides are spaced apart from each other and are substantially parallel to each other.

13. The expandable interbody device of claim 12, wherein at least two first racks and at least two second racks are operationally connected to the plurality of gears on the first side of the support structure and at least two first racks and at least two second racks that are operationally connected to the plurality of gears on the second side of the support structure, and wherein the at least two first racks and the at least two second racks on the first side of the support structure move more than the at least two first racks and the at least two second racks on the second side of the support structure when the plurality of gears are rotated in the opening direction such that the expandable interbody device is configured to asymmetrically expand.

14. The expandable interbody device of claim 1, wherein the expandable interbody device has a minimum thickness and a maximum thickness corresponding to a maximum extension position of the plurality of first and second racks, and wherein the maximum thickness is at least 150% of the minimum thickness.

15. The expandable interbody device of claim 1, further comprising a locking mechanism adapted to block rotation of the plurality of gears.

16. A method of fusing a person's spine, the method comprising:
    inserting the expandable interbody device of claim 1 between adjacent vertebral bodies; and
    rotating the plurality of gears, thereby moving the top and bottom plates away from the support structure, thereby increasing a distance between the adjacent vertebral bodies.

17. An expandable interbody device comprising:
    a support structure having a top side and a bottom side;
    a top plate positioned on the top side of the support structure;
    a bottom plate positioned on the bottom side of the support structure;
    a gear rotatably connected to the support structure, wherein the gear is rotatable relative to the support structure;
    a first rack that is operationally coupled to the top plate, wherein the first rack is operationally connected to the gear such that rotating the gear in an opening direction moves the top plate away from the support structure by moving the first rack relative to the gear;
    a second rack that is operationally coupled to the bottom plate, wherein the second rack is operationally connected to the gear such that rotating the gear in an opening direction moves the bottom plate away from the support structure by moving the second rack relative to the gear; and
    a rod operationally coupled to the first and second racks and rotationally coupled to the support structure, wherein moving the gear in an opening direction adjusts a relative orientation of the rod so that the rod pushes the top plate and bottom plate away from each other.

18. The expandable interbody device of claim 17, wherein the support structure defines a first chamber that extends through the support structure, wherein the top plate defines a second chamber that extends through the top plate, wherein the bottom plate defines a third chamber that extends through the bottom plate, wherein the first, second and third chambers are substantially aligned along a vertical axis of the expandable interbody device, and wherein the first, second and third chambers collectively define a contiguous area configured to receive bone graft material to provide bony fusion between adjacent vertebra through the expandable interbody device.

19. An expandable interbody device comprising:
    a support structure having a top side and a bottom side and defining a first chamber that extends through the support structure;
    a top plate positioned on the top side of the support structure, wherein the top plate defines a second chamber that extends through the top plate;
    a bottom plate positioned on the bottom side of the support structure, wherein the bottom plate defines a third chamber that extends through the bottom plate, wherein the first, second and third chambers are substantially aligned along the expandable interbody device and wherein the first, second and third chambers collectively define a contiguous area configured to receive bone graft material to provide bony fusion between adjacent vertebra through the expandable interbody device; and
    a first gear rotatably connected to the support structure, wherein the first gear is rotatable relative to the support structure;
    wherein the top plate, the bottom plate and the first gear are operationally coupled together such that rotating the first gear in an opening direction increases a gap between the top plate and the bottom plate;
    a rod operationally coupled to the first gear, wherein moving the the opening gear in an opening direction adjusts a relative orientation of the rod so that the rod pushes the top plate and bottom plate away from each other;
    an abutment selectively movable by rotation of the first gear, wherein the abutment is adapted to adjust the relative orientation of the rod so that the rod pushes the top plate and bottom plate away from each other, wherein the abutment includes an angled surface that determines a maximum adjustment of the relative orientation of the rod and a maximum distance between the top plate and the bottom plate.

20. The expandable interbody device of claim 19, further comprising:
    a window that extends through the support structure adapted to pass graft material through the support structure to the first chamber.

21. An expandable interbody device comprising:
    a support structure having a top side and a bottom side and defining a first chamber that extends through the support structure;
    a top plate positioned on the top side of the support structure, wherein the top plate defines a second chamber that extends through the top plate;
    a bottom plate positioned on the bottom side of the support structure, wherein the bottom plate defines a third chamber that extends through the bottom plate, wherein the first, second and third chambers are substantially aligned along the expandable interbody device and wherein the first, second and third chambers collectively define a contiguous area configured to receive bone graft material to provide bony fusion between adjacent vertebra through the expandable interbody device; and
    a first gear rotatably connected to the support structure, wherein the first gear is rotatable relative to the support structure;
    wherein the top plate, the bottom plate and the first gear are operationally coupled together such that rotating the first gear in an opening direction increases a gap between the top plate and the bottom plate;

a second gear rotatably connected to the support structure, wherein the second gear is rotatable relative to the support structure;

wherein the top plate, the bottom plate and the second gear are operationally coupled together such that rotating the second gear in an opening direction increases a gap between the top plate and the bottom plate, and wherein the first chamber is positioned between the first and second gears, wherein the first and second gears are configured to be separately rotated by a single tool that engages both the first and second gears by passing through the first gear and the first chamber.

22. An expandable interbody device comprising:

a support structure having a top side and a bottom side and defining a first chamber that extends through the support structure;

a top plate positioned on the top side of the support structure, wherein the top plate defines a second chamber that extends through the top plate;

a bottom plate positioned on the bottom side of the support structure, wherein the bottom plate defines a third chamber that extends through the bottom plate, wherein the first, second and third chambers are substantially aligned along the expandable interbody device and wherein the first, second and third chambers collectively define a contiguous area configured to receive bone graft material to provide bony fusion between adjacent vertebra through the expandable interbody device; and a first gear rotatably connected to the support structure, wherein the first gear is rotatable relative to the support structure;

wherein the top plate, the bottom plate and the first gear are operationally coupled together such that rotating the first gear in an opening direction increases a gap between the top plate and the bottom plate;

a second gear rotatably connected to the support structure, wherein the second gear is rotatable relative to the support structure;

wherein the top plate, the bottom plate and the second gear are operationally coupled together such that rotating the second gear in an opening direction increases a gap between the top plate and the bottom plate, wherein the first chamber is positioned between the first and second gears;

a first plurality of interconnected gears rotatably connected to a first side of the support structure, wherein the first plurality of interconnected gears rotate with the first gear;

a first plurality of racks coupled to the top plate, wherein the first plurality of racks are operationally connected to the first plurality of interconnected gears such that rotating the plurality of interconnected gears in the opening direction moves a first side of the top plate away from the support structure by moving the first plurality of racks relative to the first plurality of interconnected gears;

a second plurality of interconnected gears rotatably connected to a second side of the support structure opposite the first side, wherein the second plurality of interconnected gears rotate with the second gear; and a second plurality of racks coupled to the top plate, wherein the second plurality of racks are operationally connected to the second plurality of interconnected gears such that rotating the second plurality of interconnected gears in the opening direction moves a second side of the top plate away from the support structure by moving the second plurality of racks relative to the second plurality of interconnected gears.

23. The expandable interbody device of claim 22, wherein the first and second gears are configured to be separately rotated such that the relative angle between the top plate and the bottom plate can be varied.

24. The expandable interbody device of claim 22, wherein a first distance that the first side of the top plate moves relative to the support structure due to a particular angle of rotation of the first gear is different than a second distance that the second side of the top plate move relative to the support structure due to the same particular angle of rotation of the second gear.

* * * * *

UNITED STATES PATENT AND TRADEMARK OFFICE
CERTIFICATE OF CORRECTION

Page 1 of 1

PATENT NO. : 11,109,979 B2
APPLICATION NO. : 16/970490
DATED : September 7, 2021
INVENTOR(S) : Michael Craig McMains It is certified that error appears in the above-identified patent and that said Letters Patent is hereby corrected as shown below:

In the Claims

Column 9, Line 5, Claim 13 delete "that"
Column 10, Line 29, Claim 19 delete "the opening gear in an" and replace with --first gear in the--

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*